United States Patent [19]

Tuffile et al.

[11] 4,102,641
[45] Jul. 25, 1978

[54] METHOD OF DYEING HUMAN HAIR WITH REACTIVE DYES

[75] Inventors: Fred M. Tuffile, Lakeville, Mass.; Andrew J. Cunningham, Highland Lakes, N.J.

[73] Assignee: Avon Products, Inc., Suffern, N.Y.

[21] Appl. No.: 293,473

[22] Filed: Sep. 29, 1972

[51] Int. Cl.² .............................................. A61K 7/13
[52] U.S. Cl. ............................................ 8/10.1; 8/10; 8/85 R; 8/85 A; 8/88
[58] Field of Search .......................... 8/10, 10.1, 85, 88

[56] References Cited

U.S. PATENT DOCUMENTS

| | | | |
|---|---|---|---|
| 3,396,736 | 8/1968 | Shansky | 8/10.1 |
| 3,415,606 | 12/1968 | Randerbrock | 8/10.1 |
| 3,679,347 | 7/1972 | Brown | 8/10.1 |

Primary Examiner—Albert T. Meyers
Assistant Examiner—Vera C. Clarke
Attorney, Agent, or Firm—Pennie & Edmonds

[57] ABSTRACT

A process for permanently dyeing keratinous fibers with halotriazinyl reactive dyes wherein good leveling and uptake is attained. More particularly, a process for dyeing human hair comprising subjecting the fibers to sequential treatment of first applying to the fibers a halotriazinyl reactive dye at a pH of from about 4 to 6.5 and then allowing the dye to bond with the fibers at a pH of about 8 to 8.5.

7 Claims, No Drawings

METHOD OF DYEING HUMAN HAIR WITH REACTIVE DYES

BACKGROUND OF THE INVENTION

For many years people have been dissatisfied with the natural color found in keratin materials such as in human hair and have sought preparations capable of modifying their color. Numerous color modifying materials and many varied procedures for applying such materials have been developed in an attempt to formulate a coloring technique which will give good leveling properties and at the same time will have good uptake and fastness of the dye used.

Generally, there are three methods for dyeing fibers of all kinds. These being absorption, aggregation and bonding techniques. In the absorption method the dyestuff or the vehicle in which it is introduced has an electron affinity for the fiber being treated. This technique does not include true chemical bonding of dye to the fiber but relies primarily on the charge differential between the materials.

The aggregation method of dyeing involves a system of insolubility which is created inside the fiber to be dyed. The dyestuff is made fast by penetration into the fiber and the precipitation therein of the chromogenous agent. Textile type dyestuffs are normally applied by this method. In the bonding technique, a chemical bond between the dye material and the fiber is produced. Fiber reactive dyestuffs are applied by this method which makes use of a reaction between some constituent of the dye molecule and a reactive group of the fiber such as a thiol or amino group.

The use of the absorption or aggregation methods of dyeing keratin fibers has several disadvantages. One of the main disadvantages is the lack of fastness in these methods since there is no true bonding of the chromogenous agent to the fiber. It is to be observed that in a purely aggregative technique, for example, as where precipitation is employed, there cannot be bonding and the only reason the dye has any fastness at all is that some penetrates into and is left within keratin fiber which has been swollen during the treatment. Where absorption techniques are utilized with oxidative dyes, there is still no true bonding since the colored complex is not bound to the keratin fiber by true covalent bonds. The lack of permanency of the dyes used with this technique attests to its lack of fastness.

The bonding technique wherein reactive dyes are utilized has shown, in general, the properties of good uptake and fastness. The chemical bond which is formed between the dye material and the treated fiber forms a truly permanent dyed material so that some subsequent process must be performed to cause removal of the color. In the past the use of reactive dyes as a chromogenous material was limited to textile materials and the like due to the severe conditions which were needed to force the reaction to occur. More recently, reactive dyes of the class of halotriazinyl compounds have been found to be reactive with fibrous materials at less harsh conditions than were previously necessary. These dyes are, therefore, potentially useful in the cosmetic industry as colorants for human hair, but up to the present time the halotriazinyl dyes have not been used widely due to poor leveling properties. Samples made with these dyes have, in general, formed uneven coloring.

SUMMARY OF THE INVENTION

A process has now been unexpectedly found which provides a novel method for using reactive dyes as a colorant on keratin fibers such as human hair wherein good leveling properties are attained, as well as giving a high degree of fixation, good buildup, and excellent wet fastness qualities.

The process comprises the sequential steps of first applying to the hair fibers a composition containing at least one halotriazinyl reactive dye material at a pH of from about 4 to 6.5 and then allowing the dye to be bonded with the keratin fibers at a pH of about 8 to 8.5.

DETAILED DESCRIPTION OF THE INVENTION

The present invention provides a new and improved method for permanently dyeing human hair with reactive dye materials of the halotriazine class. The discussion hereinbelow is with reference to human hair as the keratinous fiber to which this cosmetic dye process is highly suited.

There are known sites in keratinous fibers which will react with various chemical moieties to form a truly covalently bonded product. In the past, hair was first subject to a pretreatment with a disulfide reducing agent. The cystine linkage of the fiber thus being broken to form a swollen, more pliable fiber having sulfhydryl groups which were the primary sites of reaction. These sulfhydryl groups were usually formed under conditions which can cause depilation.

Up to the present it has been thought that reactive dyes could only be used commercially where the hair has been first pretreated with a reducing composition as stated above. Even when this pretreatment was used the resultant dyed fibers showed poor leveling properties.

It has been presently unexpectedly found that by applying reactive dyes to the hair under the conditions disclosed below, the fibers can be permanently dyed within commercially acceptable conditions without pretreatment and will result in a product having superior leveling than heretofore known.

The fiber reactive dyes which are useful in the process of this invention are dyestuffs containing a halotriazinyl group such as monochlorotriazine, dichlorotriazine and the like. These halogenated dyestuffs contain one or more solubilizing groups as well as a dye substituent. These dyes bond with one of the reactive groups of the keratin fiber, such as with an amino group. It is believed that a true covalent bond is formed with the reactive sites in the keratinous fiber and although the exact process is not known, it is believed to occur generally by alkylation of the materials.

The halotriazinyl compounds which may be used in the process of this invention are well known to those skilled in the art. They include the monohalotriazines and the dihalotriazines. The triazines are the 1,3,5-triazines and are substituted with at least one residue of a dyestuff molecule. The residue of the dyestuff may be of any known dyestuff series but preferably they are residues of dyestuffs of the azo, which may be the monoazo or polyazo, nitro, anthraquinone or phthalocyanine series and which preferably contain at least one water solubilizing group such as a carboxylic, alkyl sulfonyls, sulphamyls and sulfonic acid groups. If desired, the dyestuff molecules may also contain coordinately bonded metals such as coordinately bound copper, chromium or cobalt. Numerous examples of halo-s- triazinyl dyestuff materials are described in U.S. Pat. Nos. 3,118,869 and 2,978,289 as well as 3,121,712.

In carrying out the process, the dye material is applied to hair at a pH of from about 4 to about 6.5. At this pH range the dye material has been found to have good distribution properties which are not changed upon pH adjustment thus giving the dyed end product of the process improved leveling properties. Normally, the dye composition, as applied to the hair, will have a pH within the desired range. If this is not so, or alternatively, if a different pH within the range described is desired, a buffer material such as acetic acid-sodium acetate (pH of 4.6 at 0.1 molar concentrations), secondary sodium citrate (pH of 5.0 at 0.1 molar concentrations) and the like or, alternately, a small amount of a weak acid or alkali may be incorporated in the dye composition to produce the desired pH. The dye material is allowed to remain on the hair for a period of approximately 5 to 20 minutes with from 8 to 12 minutes being the preferable range of application. The length of application of the dye material will depend upon the type of dye used, as well as the type of solution and application used and this is readily determined, as by the use of test swatches.

The second step of the process involves the reacting of the distributed colorant with the hair. This second step occurs at a pH in the range of about 8 to 8.5. At this range it has been found that the dye which has been previously well distributed will react with the keratin fibers and thus form a truly permanent bond with said fibers. The length of time of application at the more alkaline pH is from about 10 minutes to about 20 minutes in duration. Times which are somewhat shorter or somewhat longer may be applicable in some cases. The exact time of application will depend upon the particular dye which is being used, the method of application and the particular texture of the hair being dyed; again details which are easily determined by those skilled in the hair coloring art.

This latter pH range can be attained by the addition of a suitable alkaline material having an ionization constant within the proper range. Generally, any mild alkaline material which is known to those skilled in the art may be used. Mild alkaline materials such as alkyl amines and alkanolamines and the like have been found useful in this application. The amount necessary is normally of catalytic quantities and can be calculated for the particular composition being applied. One such compound that has been found to give excellent results is triethanolamine which has an ionization constant of $8.1 \times 10^{-7}$, is a mild base and has low heat of solution.

While the leveling and reacting steps can be performed in a distinctly two-step process as discussed, the application may be performed in one step wherein the alkaline material is incorporated in the initial solution used. In this one-step process, the alkaline material must be in such a form as to not be active for a sufficient period of time to allow the desired leveling properties to first occur. This can be accomplished by microencapsulating the basic material with a water soluble material in which microcapsules are mixed with the dye material just prior to application. The thickness of the microencapsulation coating and the particular coating material are varied to give the duration of inactivation of the alkaline material that is required. The process of microencapsulation forms no part of the instant invention, as such process is old and the techniques thereof are well known as set forth in U.S. Pat. Nos. 3,418,656 and 3,418,250.

The halotriazinyl dye, as described herein, is applied to the hair, in general, in the form of an aqueous solution such as in combination with an aqueous shampoo composition. The aqueous solution being readily applicable to the keratin fibers, remains on the keratin fibers for the length of time necessary for proper leveling. The hair is then rinsed with warm water and may then be washed with any commercial shampoo in order to remove residual material. Additional solvents such as alcohols may, when found necessary, be incorporated in the aqueous solution.

The various halotriazinyl reactive dyes may be applied singularly or in combination with each other, depending upon the exact color or color combination which is desired. In addition various fillers, buffers, solvents, detergents, perfumes, stabilizers and the like may be used in combination with the solution applied to the keratin fiber so long as the pH limitations are met. The use of these various additional ingredients will depend upon the specific mode of application, the specific type of keratin fiber and dyestuff being used as well as other variables known to those skilled in the art.

The following examples are set forth for the purposes of illustration only and are not to be construed as limitations on the present invention except as set forth in the appended claims. All parts and percentages are by weight unless otherwise indicated.

EXAMPLE I

An aqueous shampoo base is prepared of the following composition:

| | |
|---|---|
| FORMALIN | 0.025 |
| HYDROXYETHYL CELLULOSE | 0.750 |
| BTC 50 (BENZALKONIUM CHLORIDE SOLUTION) | 3.000 |
| LMDA (70:30) LAUROYL-MYRISTOYL DIETHANOLAMIDE) (COCOYL BETAINE) or | 2.000 |
| CULVERAM CADG (COCOAMIDOPROPYLDIMETHYL BETAINE) | 3.000 |
| BUTYLATED HYDROXYANISOLE | 1.000 |
| RESORCINOL | 1.000 |
| PERFUME | 0.500 |
| n-PROPANOL | 10.000 |
| $H_2O$ q.s. | 100.000 |

To the shampoo solution is added 5.0 parts of a dichloro-s-triazine dye having the formula:

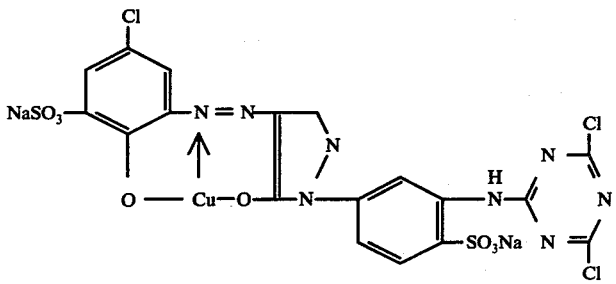

The shampoo is adjusted to a pH of 5.5 with a 10% solution of acetic acid. The shampoo is then applied to human hair and allowed to remain thereon for approximately 10 minutes.

A 100 parts aqueous solution containing 1 part of triethanolamine is applied to the hair raising the pH of the coloring shampoo composition to 8. The coloring composition is allowed to remain on the hair for an additional 15 minutes.

The hair is rinsed with warm water and then with commercial shampoo. Upon examination the resultant golden brown dyed hair shows good leveling and wet fastness of the dye. There is substantially no skin staining.

EXAMPLE II

To an aqueous shampoo composition as described in Example I is added 10 parts of 4,6 dichoro-1,3,5-triazinyl-(2)-4-amino-2-methylphenyl-(1)-1-hydroxynaphthalene-4-sulfonic acid in combination with a 0.1 M solution of acetic acid-sodium acetate. The resultant dye containing composition has a pH of 4.6. The composition is applied to the hair in the normal manner and allowed to remain thereon for 10 minutes. The hair is then treated with a 1% solution of triethanolamine. The coloring composition is allowed to remain on the hair for an additional 15 minutes.

The hair is rinsed free of the dye composition with warm water and then with a commercial shampoo. Upon examination the resultant dyed hair shows good leveling and wet fastness of the dye. There is substantially no skin staining.

EXAMPLE III

A comparative example is made wherein an aqueous shampoo solution having a dichlorotriazinyl dye as in Example II but wherein no buffer solution is used and the solution has a pH initially above 6.5 and to which a 1% aqueous solution of triethnaolamine is added giving a resultant pH of 8.1. This solution is applied to the hair for approximately 15 minutes.

The hair is then rinsed of the dye composition with warm water and finally with a commercial shampoo. Upon examination the resultant dyed hair is less evenly distributed and there is less brilliance to the dyed color in comparison to Example II.

EXAMPLE IV

An aqueous shampoo solution similar to that used in Example I is combined with 10 parts of a triazinyl compound having the formula

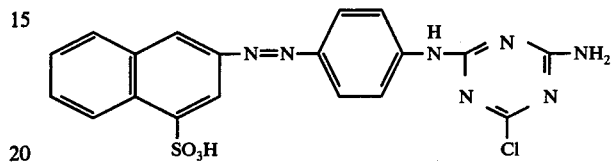

and 10 parts of triethanolamine is microencapsulated in a water soluble wax of a thickness which will substantially dissolve in about 10 minutes.

The aqueous shampoo-dye solution having an initial pH of approximately 5.0 is applied to the hair and allowed to remain for 25 minutes. A sample of the shampoo-dye solution tested after 15 minutes shows a pH of 8.0.

The hair is rinsed free of the dye solution with warm water and finally with a commercial shampoo. The hair shows, upon examination, good uptake and leveling of the dye used and has good wet fastness.

It will be understood that it is intended to cover all changes and modifications of the examples of the invention herein chosen for the purpose of illustration which do not constitute departures from the spirit and scope of the invention.

What is claimed is:

1. A process of dyeing human hair comprising applying to the hair fibers in an aqueous solution and at a pH of about 4 to 6.5 an effective coloring amount of a halotriazinyl compound, which compound contains a dye residue group and a water solubilizing group for a period of time sufficient to allow good leveling of said dye, subsequently applying to the hair an aqueous solution containing sufficient amounts of an alkaline compound having an ionization constant sufficient to adjust the pH to from about 8 to 8.5 and maintaining said pH range of about 8 to 8.5 for a period of time sufficient to allow reaction of the dyestuff with the hair fibers, and then rinsing the hair fibers.

2. A process according to claim 1 wherein the hair fibers are living human hair.

3. A process according to claim 1 wherein the halotriazinyl compound contains monohalotriazinyl group.

4. A process according to claim 1 wherein the halotriazinyl compound contains a dihalotriazinyl group.

5. A process according to claim 1 wherein the alkaline compound is triethanolamine.

6. A process according to claim 1 wherein the aqueous dye solution remains on the hair at a pH of about 4 to 6.5 for a period of time of from about 5 minutes to about 20 minutes.

7. A process according to claim 6 wherein the aqueous dye solution remains on the hair fibers at a pH of from about 8 to about 8.5 for a period of time ranging from about 10 minutes to about 20 minutes.

* * * * *